(12) United States Patent
Kesling

(10) Patent No.: US 7,025,591 B1
(45) Date of Patent: Apr. 11, 2006

(54) SELF-LIGATING ORTHODONTIC APPLIANCE

(75) Inventor: Andrew C. Kesling, LaPorte, IN (US)

(73) Assignee: TP Orthodontics, Inc., Westville, IN (US)

( * ) Notice: Subject to any disclaimer, the term of this patent is extended or adjusted under 35 U.S.C. 154(b) by 286 days.

(21) Appl. No.: 10/682,353

(22) Filed: Oct. 9, 2003

(51) Int. Cl.
*A61C 3/00* (2006.01)

(52) U.S. Cl. .......................... 433/10; 433/11
(58) Field of Classification Search .................. 433/10, 433/11, 8, 13, 16
See application file for complete search history.

(56) References Cited

U.S. PATENT DOCUMENTS

| | | | | |
|---|---|---|---|---|
| 5,224,858 A | * | 7/1993 | Hanson | 433/10 |
| 5,474,445 A | * | 12/1995 | Voudouris | 433/10 |
| 5,711,666 A | | 1/1998 | Hanson | |
| 6,257,883 B1 | * | 7/2001 | Voudouris | 433/11 |
| 6,554,612 B1 | | 4/2003 | Georgakis et al. | |
| 6,582,226 B1 | | 6/2003 | Jordan et al. | |
| 6,659,767 B1 | * | 12/2003 | Abels et al. | 433/10 |

* cited by examiner

*Primary Examiner*—Ralph A. Lewis
*Assistant Examiner*—Casey Donahoe
(74) *Attorney, Agent, or Firm*—Lloyd L. Zickert

(57) ABSTRACT

A self-ligating orthodontic appliance including a base, one or more pivotally and movably mounted jaws on the base, and a spring member actuable to coact with the base and jaws and selectively move the jaws between open and closed positions.

19 Claims, 8 Drawing Sheets

SELF-LIGATING ORTHODONTIC APPLIANCE

This invention relates in general to an orthodontic appliance for connecting an archwire to a tooth, and more particularly to a self-ligating orthodontic bracket mountable on a tooth that may be opened for insertion or removal of an archwire and closed for retaining the archwire on a tooth, and still more particularly to a self-ligating bracket having at least one slidable and pivotal jaw connected to a spring and movable between open and closed positions by applying a force to the spring.

BACKGROUND OF THE INVENTION

Heretofore, it has been well known to provide self-ligating orthodontic brackets for use in orthodontic treatment of patients that eliminate the need to apply ligatures for retaining an archwire on a bracket. These brackets are intended to enhance the efficiencies of orthodontic treatment and also eliminate the problem sometimes encountered in ligature failure particularly with respect to use of elastomeric ligatures. Moreover, it is known that some self-ligating brackets, whether adapted for use labially or lingually, eliminate the need for tie wings.

It has also been known to provide self-ligating brackets that will release the archwire from the archwire slot whenever the forces on an archwire exceeds a certain minimum value, such as disclosed in U.S. Pat. No. 6,554,612 and U.S. Pat. No. 6,582,226.

Another example of a self-ligating bracket having a sliding archwire retaining member is disclosed in U.S. Pat. No. 5,711,666.

Heretofore known self-ligating brackets with complex mechanical configurations have a tendency to excessively trap food particles, and irritate the tissues of the mouth. Some are difficult to open and close for insertion and removal of the archwire, and are unreliable to withstand the masticatory forces of the mouth.

SUMMARY OF THE INVENTION

The self-ligating orthodontic appliance of the present invention provides a bracket having a configuration that minimizes the trapping of food particles and enhances patient comfort. Further, the self-ligating bracket of the present invention is compact and easy to operate between open and closed positions for insertion or removal of an archwire.

The self-ligating bracket of the invention includes a base adapted to be attached to a mounting pad or band, at least one jaw hingedly mounted on the base for selective movement between open and closed positions and defining an archwire slot in closed position, and a spring member engaging the jaw or jaws and coacting with the mounting of the jaws on the base to be engageable by a suitable tool for opening the jaws and allowing an archwire to be inserted or removed. The spring member is engageable by the archwire as the archwire is inserted, and application of a force to the archwire causes closure of the jaws.

Where the self-ligating bracket of the invention includes a pair of jaws, they are configured so that when they are in closed position, they coact to define an archwire slot for an archwire, and if the slot is rectangular for a rectangular archwire, a torquing force can be applied by the archwire to a tooth.

The jaws include hinge lugs that mate and coact with hinge lugs on the base and hinge pins. The hinge is similar to a piano hinge. The hinge pins are carried by lugs while coacting lugs on the jaws include kidney-shaped openings receiving the hinge pins such as to allow the jaws to slidably move relative to the base and pivot relative to the base during opening and closing of the bracket. The sliding movement locks or unlocks the jaws.

In order to further insure the locking of the jaws in closed position against opening, locking teeth may be provided on the base and the lugs of the jaws to interengage when the jaws are in closed and retaining position.

Preferably, the base is provided with a mounting pad in the form of cured plastic material of a suitable polymer resin to enable the bracket to be bonded to a tooth with a suitable bonding material. A foil/mesh bonding pad may also be attached to the base to allow bonding of the bracket to a tooth. It should also be appreciated that a band may be attached to the base for banding the bracket to a tooth. With respect to providing a cured polymer resin bonding pad, it should be appreciated that the bracket may also be provided with an uncured light-curable layer of polymer resin and shipped by the manufacturer to a user so that it may be directly mounted onto a tooth and where the uncured layer may be cured by a suitable light source to securely bond the bracket to a tooth.

Moreover, it should be appreciated with respect to the bracket of the invention to be adapted for the straight-wire technique and various prescriptions, functions or values may be built into the mounting pad and/or bracket configuration to provide tip or angulation, torque, rotation, and in/out values according to well known prescriptions for various systems. In this respect, the configuration of the mounting pad and the orientation of the bracket on the pad may attain a desired value, and/or the bracket may be rhomboidally shaped in the buccolingual (side) profile and/or labiobuccal (front) profile. Further, the rotation function or value and/or other functions may be built into the configuration of the archwire slot. For simplicity, the values for the bracket illustrated herein are zero.

It is therefore an object of the present invention to provide a new and improved self-ligating orthodontic appliance for use in the orthodontic treatment of patients that can be economically manufactured and easily handled by a professional user during treatment.

Another object of the present invention is to provide a new and improved self-ligating orthodontic bracket configured to minimize areas for trapping food particles and to enhance patient comfort.

A further object of the present invention is in the provision of a self-ligating orthodontic bracket having a pair of jaws pivotally and movably mounted to a base and connected to a spring member for coacting to drive the jaws to be selectively opened for insertion or removal of an archwire and closed for retention of an archwire.

A still further object of the present invention is to provide a new and improved self-ligating orthodontic bracket that will enhance the treatment of patients and reduce chair time for the professional user.

Other objects, features and advantages of the invention will be apparent from the following detailed disclosure, taken in conjunction with the accompanying sheets of drawings, wherein like reference numerals refer to like parts.

DESCRIPTION OF THE INVENTION

Figure 1:
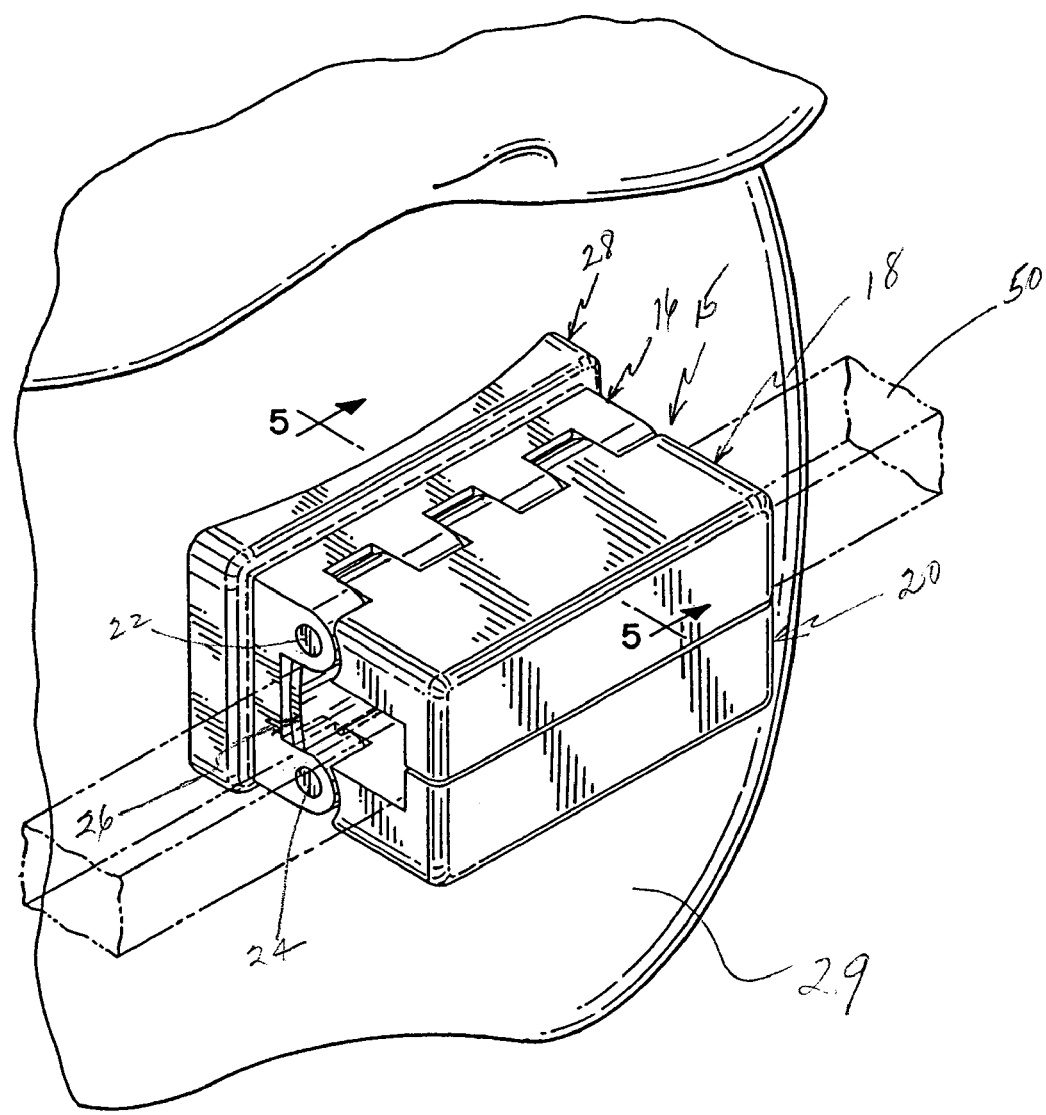
FIG. 1 is an enlarged perspective view of the self-ligating orthodontic bracket of the present invention with a plastic bonding pad and mounted on a tooth, and illustrating the bracket in closed position for retaining a rectangular archwire that is shown in phantom.
Figure 2:
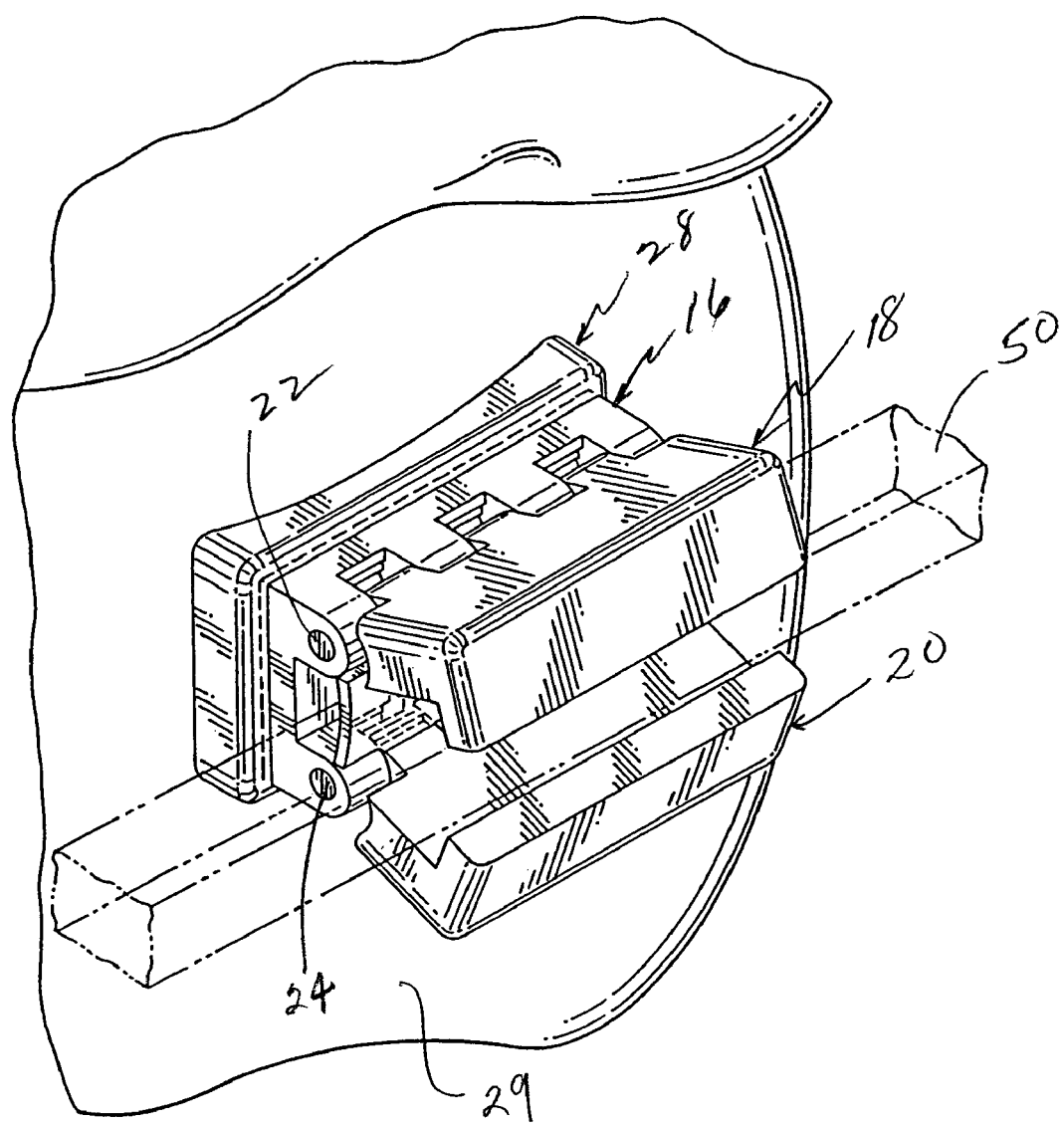
FIG. 2 is an enlarged perspective view of the bracket of FIG. 1 and showing the jaws in open position for removal or insertion of an archwire and showing the archwire in phantom.
Figure 3:
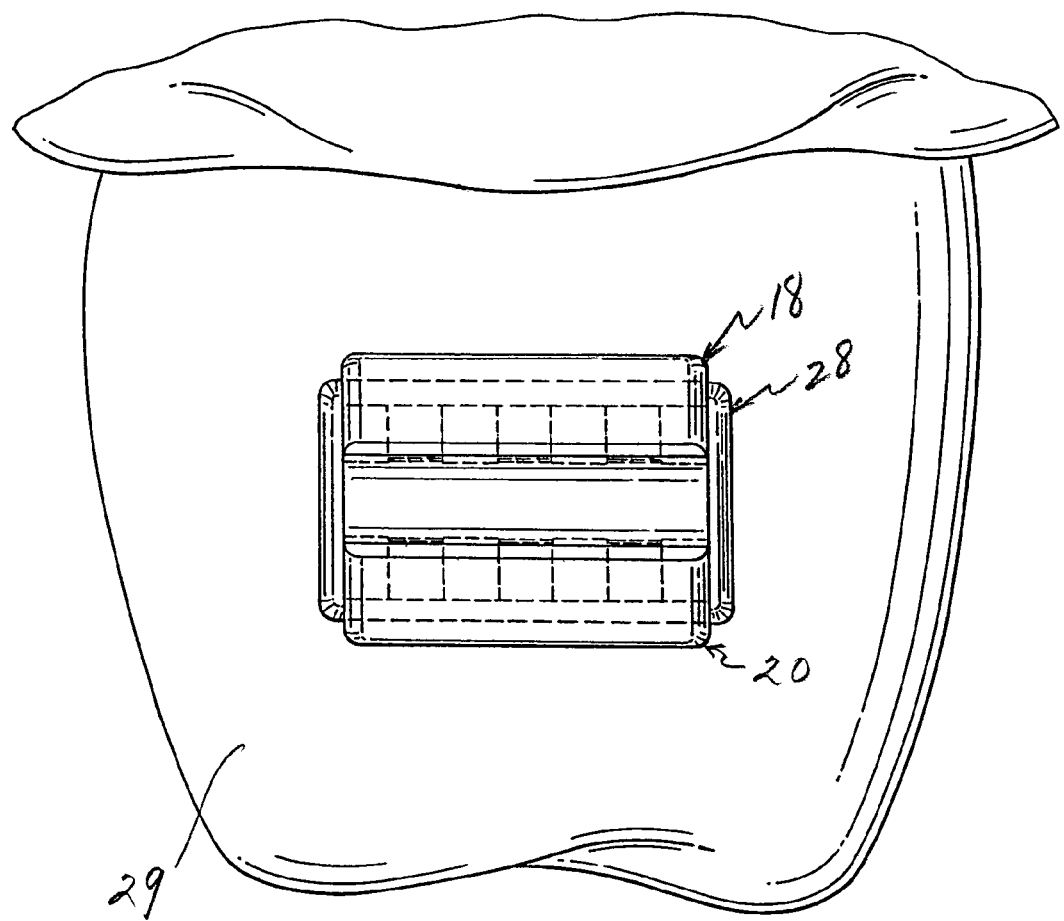
FIG. 3 is an enlarged front elevational view of the bracket of FIGS. 1 and 2 showing the jaws of the bracket in open position and underlying structure in dotted lines.

Referring now to the drawings, and particularly to FIGS. 1 to 4, the self-ligating bracketing of the present invention, generally indicated by the numeral 15, includes generally a base 16, a pair of jaws 18 and 20 hingedly mounted on the base for slidable and pivotal movement, hinge pins 22 and 24 connected to the base and coacting with the jaws, and a spring member 26.

The bracket of the invention, where shown mounted on a tooth in FIGS. 1 to 3 and 5 to 8, includes a polymer resin bonding pad 28 bondable to the outer surface of a tooth at the labial. It will be appreciated that the bonding pad is preferably molded to the base 16 and serves to be adhesively bonded to a tooth such as the labial face of a tooth 29. While the bracket of the invention is preferably labially mounted on teeth, it should be appreciated that it could be structured for mounting lingually if so desired. Further, it should be appreciated that while the mounting pad of the bracket is preferably a polymer resin mounting pad such as disclosed in copending application Ser. No. 10/285,742 filed Nov. 1, 2002, also owned by the assignee of the present application, the base could be attached to a foil/mesh bonding pad for bonding to a tooth or to a band for banding to a tooth.

It should be further appreciated that the bracket of the invention may be made of metal, whether it is cast or machined, or it may be made of ceramic or plastic. Moreover, it should be appreciated that the base may be made of metal, while the jaws could be made of ceramic or plastic in order to enhance the aesthetics of the bracket. Likewise, the hinge pins and the spring may also be made of metal or a suitable plastic.

Further, as above mentioned, it should be appreciated that the configuration of the bracket and/or mounting pad may be such as to provide tip or angulation, torque, rotation, or in/out compensation functions or values in accordance with the usual prescriptions or systems desired by users. One or more of the functions may be incorporated in any one bracket. Further, the bracket, together with the mounting pad, may be rhomboidally shaped along the buccolingual (side) profile to produce a torque value, or along the labiobuccal (front) profile to produce a tip or angulation profile.

While the bracket of the invention is illustrated as having a rectangular slot for receiving a rectangular archwire, it will be appreciated that a round archwire could be retained by the bracket in such a slot if desired. Round archwires are often used in early stages of treatment, while rectangular archwires are used in the final stages of treatment in order to provide final positioning of the teeth. Further, the shape of the archwire slot could be other than rectangular if desired.

Figure 4:
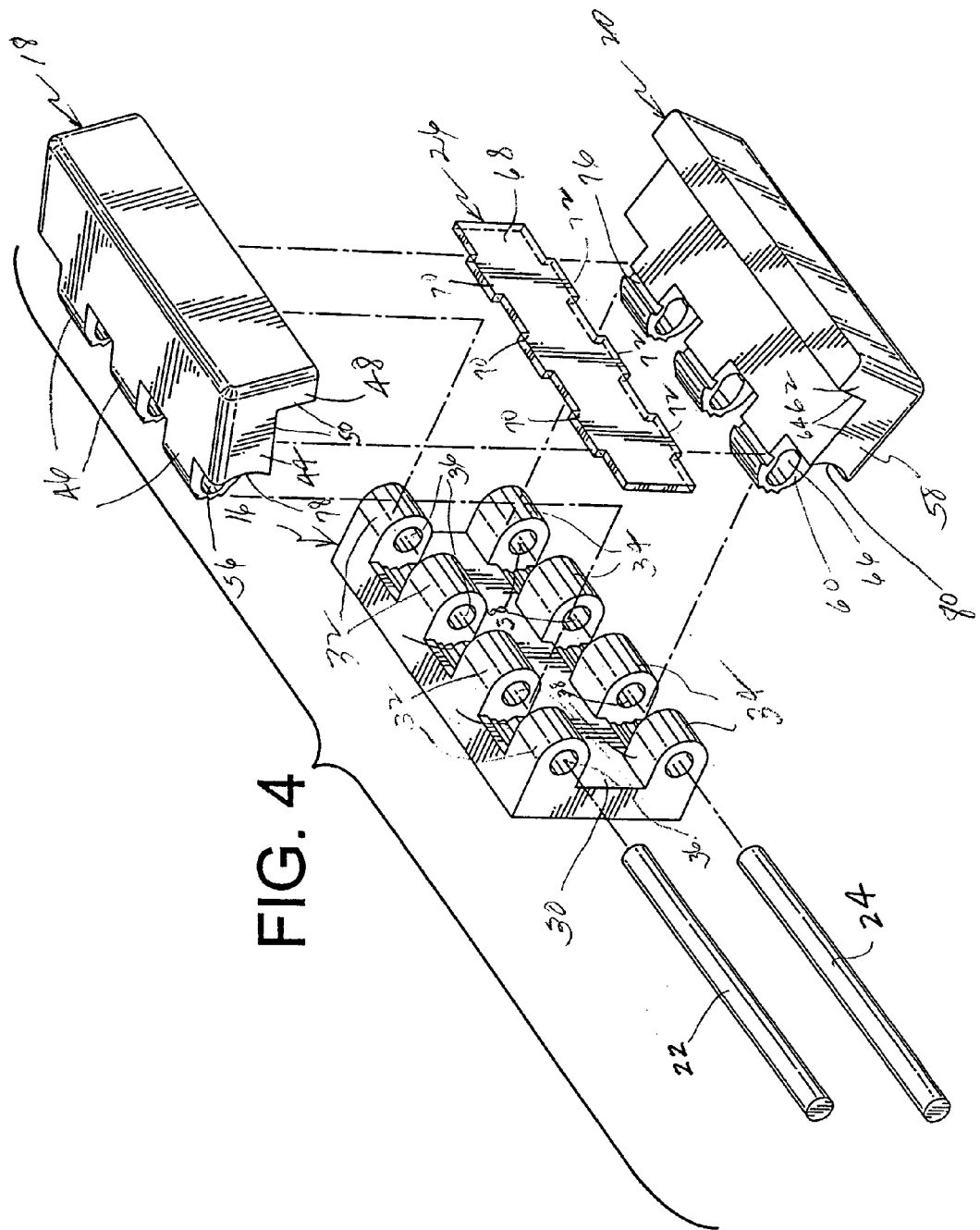
FIG. 4 is an enlarged exploded perspective view of the bracket of the present invention without a mounting pad to show the configuration of the bracket parts.

The base 16 of the bracket, as particularly seen in FIG. 4, includes a base plate 30 having a series of spaced apart lugs or ears 32 at the gingival end of the base plate and in opposing relation a series of lugs or ears 34 at the occlusal end of the base plate. The lugs 32 are spaced from the lugs 34 but preferably in identically opposite positions on the base plate 30. Each of the lugs or ears 32 includes hinge pin bores or holes 36, while each of the lugs 34 includes hinge pin bores or holes 38. When assembling the bracket parts as further explained below, the hinge pin holes 36 will receive a hinge pin 22, while the hinge pin holes 38 will receive a hinge pin 24.

Each of the jaws 18 and 20 is L-shaped and provided with lugs or ears that coact with the lugs or ears on the base. These jaws are identical, but placed in opposing relation when mounted on the base. The upper or gingival jaw 18 includes a leg 44 having lugs or ears 46 at one end and an arm 48 at the other end extending substantially perpendicular to the leg 44 such that an L-shaped face 50 is defined for contact with the rectangular archwire as shown by the rectangular archwire 52 in phantom in FIG. 1. Each of the lugs or ears 46 includes a hinge pin opening 56 configured to allow movement of the jaw laterally and pivotally with respect to the base, as further explained below. The openings are substantially kidney-shaped.

The opposing or occlusal jaw 20 is essentially identical to the jaw 18 but functions oppositely to the jaw 18, while both jaws coact to open or close the bracket and collectively define a rectangular archwire slot when closed. The jaw 20 includes a leg 58 having ears or lugs 60 at one end and an arm 62 at the other end extending perpendicular to the leg to coact with the leg and form an L-shaped face 64. Hinge pin openings or holes 66 are provided in the lugs 60. The shape of the openings is substantially kidney-shaped to permit the jaw to have a movable and pivotal relation with respect to the base. The pin openings 36 align with each other axially as do the pin openings 38 on the base. Similarly, the pin openings 56 align with each other on the jaw 18, while the pin openings 66 on the jaw 20 align with each other.

Figure 5:
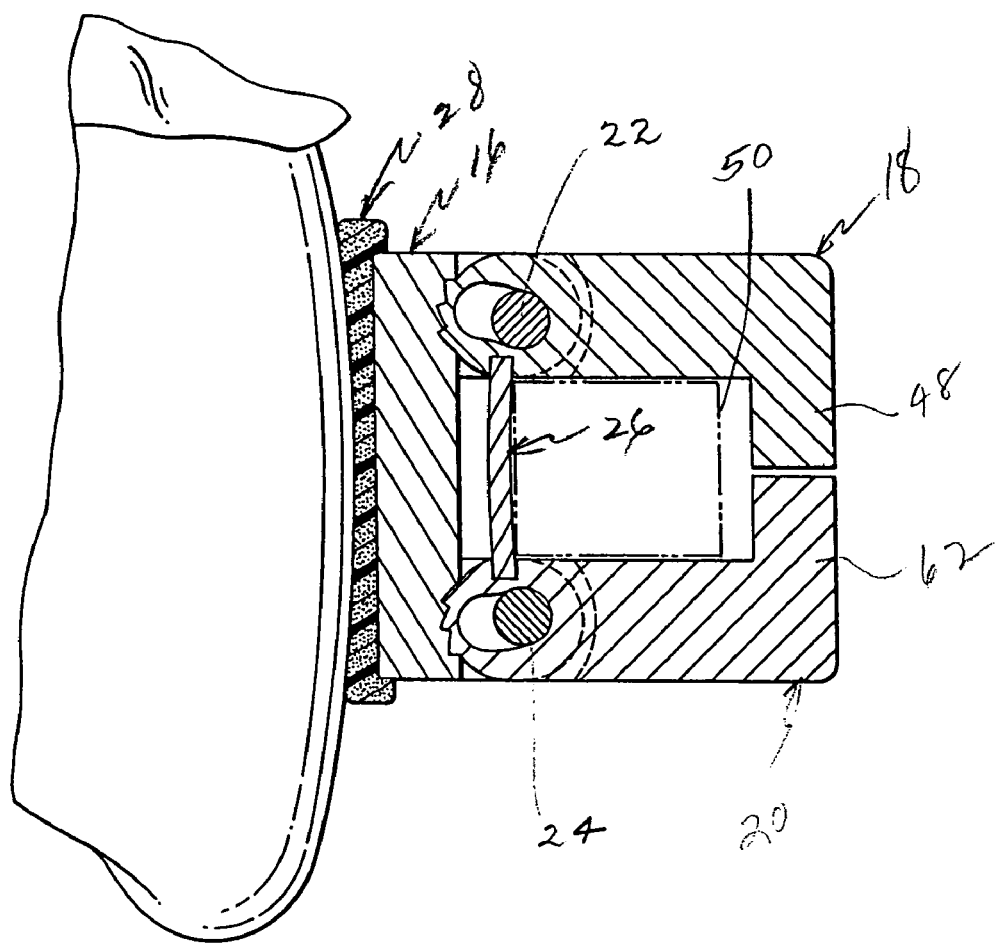
FIG. 5 is an enlarged vertical sectional view taken through the bracket of the invention with an archwire in phantom, and taken substantially along the line 5—5 of FIG. 1 which shows the bracket closed to retain an archwire.
Figure 6:
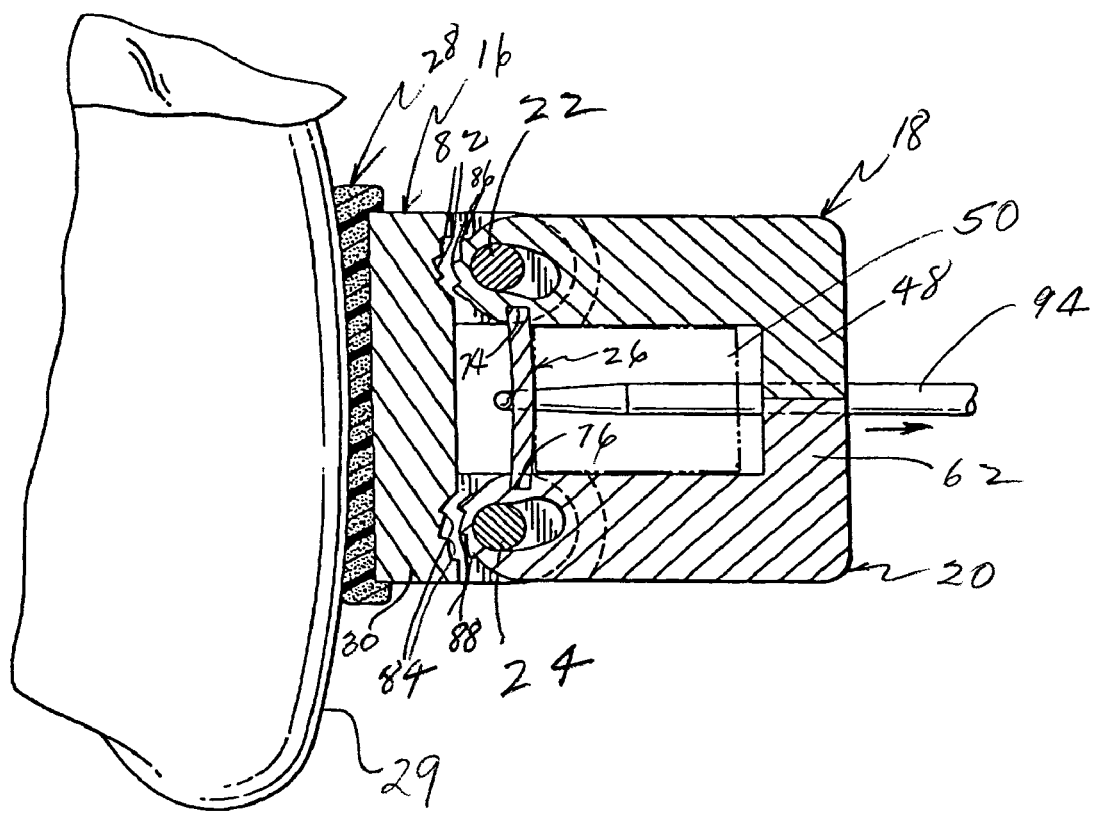
FIG. 6 is an enlarged vertical sectional view of the bracket to show the jaws slidably moved in an intermediate position during the opening cycle, and showing the application of a tool to the spring.
Figure 7:
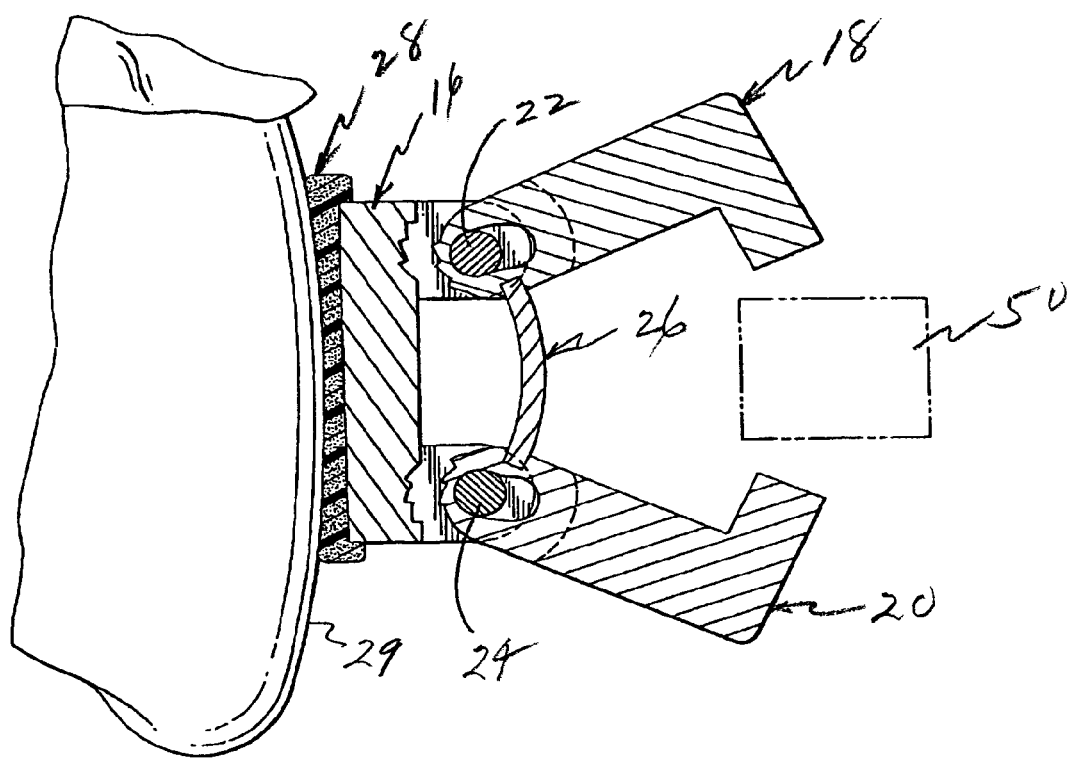
FIG. 7 is an enlarged vertical sectional view of the bracket with the jaws in fully open position to easily allow the insertion or removal of an archwire.
Figure 8:
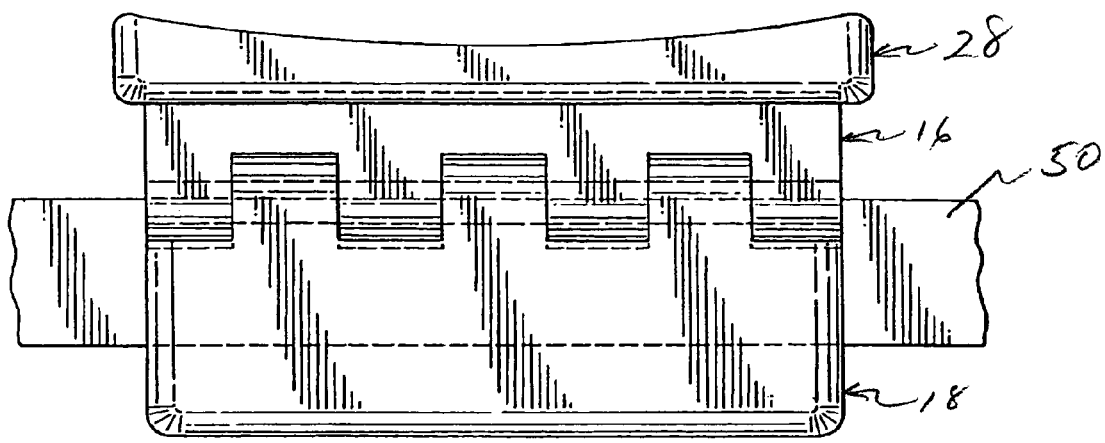
FIG. 8 is an enlarged top plan view of the bracket of the invention with the jaws in closed position and showing some underlying parts in dotted lines and an archwire retained by the archwire slot formed by the jaws.

The spring 26 includes an elongated flat body 68 and tangs 70 and 72 at opposite edges engageable in slots formed in the lugs or ears of the jaws, as seen particularly in FIGS. 5 to 7. The tangs 70 are received in slots or notches 74 at the inwardly facing side of the lugs 46, while slots or notches 76 of the jaw 20 receives tangs 72 of the spring. Between the lugs 46 on the jaw 18 and the lugs 60 on the jaw 20 and adjacent thereto and at the same ends of the legs 44 and 58, arcuately formed surfaces 78 and 80 are formed to accommodate the arcuately formed ends of the lugs 32 and 34 on the base 16.

Locking teeth or serrations are provided on the base plate 30 of the base 16 and the ends of the lugs of the jaws to serve to assure locking of the jaws when in closed position to resist opening of the jaws due to the masticatory forces generated during chewing. More particularly, as seen in the figures and particularly in the vertical sectional views 5, 6 and 7, teeth or serrations 82 are provided on the base plate 30 between the lugs 32, while teeth or serrations 84 are provided on the base plate 30 between the lugs 34. Coacting with the teeth 82 on the base plate are teeth or serrations 86 on the ends of the lugs 46 of the jaw 18. Coacting with the teeth 84 on the base plate 30 are teeth or serrations 88 on the ends of the ears 60 of the jaw 20. The teeth may be slanted in either direction or not at all. Alternatively, the interengaging teeth may be located on the base plate lugs and the arcuate faces 78 and 80 on the jaws.

When the jaws, hinge pins, and spring are assembled with the base, preferably the hinge pins, which extend through the holes in the ears on the base and the holes in the ears on the jaws, are fitted to the base such that they cannot be removed. It is not necessary that the pins be rotatable in the holes on the base as they serve to provide anchorage for the ears of the jaws. The tangs of the spring are preferably connected to the slots or notches in the ears of the jaws. For example, the tangs may be adhesively bonded, staked or tack-welded to the ears. It is also possible that the spring may be cast integrally with the casting of the lugs.

Figure 9:
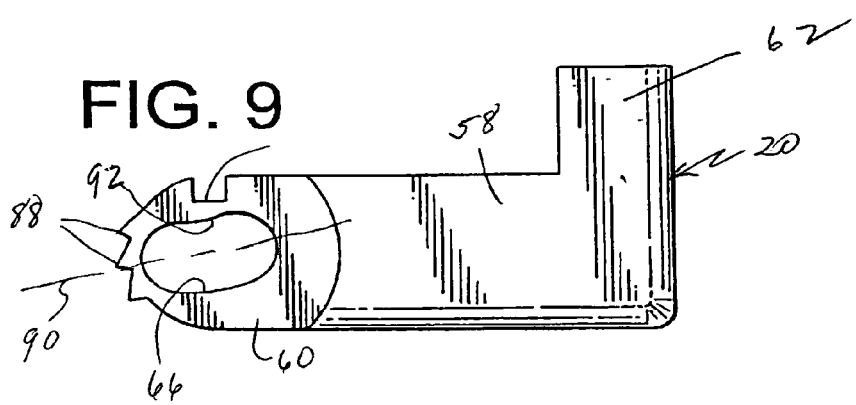
FIG. 9 is a greatly enlarged side elevational view of one of the jaws of the bracket of the invention.
Figure 10:
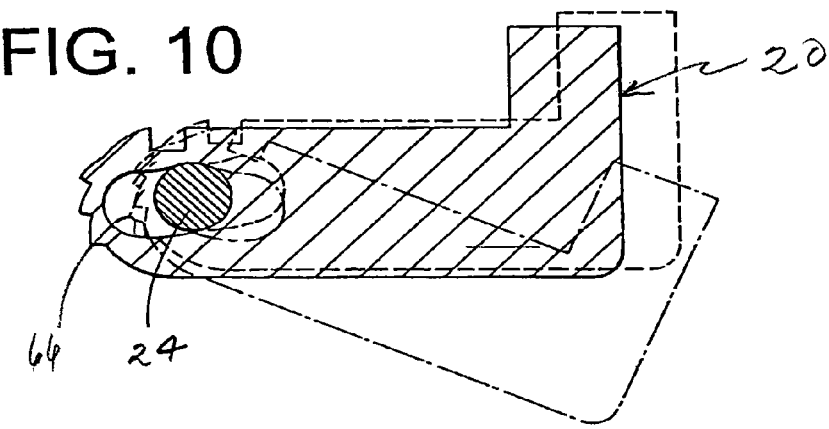
FIG. 10 is an enlarged fragmentary sectional view of a jaw illustrating the series of movable and pivotal positions of the jaw between open and closed positions.

The operation of the bracket between open and closed positions is particularly illustrated in FIGS. 5, 6 and 7, where in FIG. 5 the jaws of the bracket are shown in closed and locked position, and in FIG. 6 the jaws are shown slidably moved to an intermediate position during the opening cycle, and in FIG. 7 the jaws are pivoted to the fully open position. In the closed position the jaws retain the archwire in the archwire slot, while in the open position the jaws allow the archwire to be inserted or removed. Starting with the closed position in FIG. 5, it will be particularly noted that the ends of the jaw arms 48 and 62 are slightly spaced apart to facilitate the opening and closing of the jaws as they move along and pivot on the hinge pins 40 and 42. A greatly enlarged view of the jaw 20 is shown in FIG. 9 to emphasize the shape and orientation of the pin hole 66 of an ear 60. As above mentioned, the pin hole is kidney-shaped, and when viewing the longitudinal axis of the pin hole as indicated by the numeral 90 in FIG. 9, the axis is inclined relative to the leg 58 toward the arm 62.

The kidney-shaped openings of the jaw lugs include a bump or node 92 centrally between the opposite ends of the opening and configured such that the hinge pin 24 will be disposed on one side of the bump when the jaw is in closed position and on the other side of the bump when the jaw is in open position. These positions apply to all of the ears of each of the jaws, but for clarity will only be described relative to the ears 60 of the jaw 20. The elongated kidney-shaped hole 66 may be considered as a cam hole, and bump 92 may be referred to as a cam lobe where the hinge pin 24 with the jaw in closed position is at the top of the cam opening, while in the open position the hinge pin is in overcenter position at the bottom of the cam opening. Thus, the configuration of the kidney-shaped opening allows slidable movement of the jaw along the axis 90 and pivotal movement when the ears of the jaws are positioned such that the pins are at the bottom of the cam openings.

The spring moves away from the base during opening of the jaws and toward the base during closing of the jaws and in each position respectively holds the jaws in open or closed position. Manipulation of the spring 26 causes operation of the jaws. Opening of the jaws is produced by use of a tool such as a dental explorer 94, as seen in FIG. 6, to engage against the underside of the spring 26 and apply a force outward of the bracket. The force initially causes the spring to buckle and then the jaws to slide outwardly away from the base 16 as the cam openings in the jaw lugs move overcenter of the hinge pins. Also, the locking teeth on the base and the jaw lugs disengage. When the jaws reach the position where the bottom ends of the cam openings or slots of the jaw lugs align with the hinge pins as shown in FIG. 7, the spring causes the jaws to open fully and allow easy insertion or withdrawal of the archwire.

Closing of the jaws to form the archwire slot for connecting the archwire to the bracket is produced by inserting the archwire to engage against the spring and then applying pressure on the archwire on opposite sides of the bracket to drive the spring inwardly toward the base of the bracket, and causing first the pivoting of the jaws inwardly toward each other and then sliding of the jaws along the hinge pins into the closed position, as shown particularly in FIG. 5, where the jaws are locked in overcenter position as to the cam holes and hinge pins and in closed position by the spring with the teeth in matching engagement to fully retain the archwire on the bracket. Again, the slots move overcenter of the hinge pins. Because there is a slight movement of the jaws toward each other during the opening cycle, clearance is provided between the ends of the jaw arms, as shown in exaggerated form in FIG. 5, so that they will be able to come toward each other during that sliding movement of the jaws until the lug slots move overcenter relative to the hinge pins. It will be appreciated that a tool could be applied at either or both sides of the bracket to engage under the spring for exerting a force to open the jaws while closing of the jaws is accomplished by applying a force to the archwire to drive the spring toward its inner closed position, as shown in FIG. 5.

The outer corners and surfaces of the jaws are suitably rounded and smooth in order to eliminate any sharp edges and enhance patient comfort. It will also be appreciated that when the jaws are in closed position, food particles will just move on over the smooth surface of the jaws and not become lodged in any cavities.

It will be understood that modifications and variations may be effected without departing from the scope of the novel concepts of the present invention, but it is understood that the invention in this application is to be limited only by the scope of the appended claims.

The invention is hereby claimed as follows:

1. An orthodontic appliance for receiving an archwire comprising a base, at least one jaw member pivotally and movably mounted on the base between open and closed positions, and substantially flat spring means for coacting with the jaw to selectively lock the jaw into closed position and define with the base an archwire slot to lock the archwire to the bracket or in open position to allow the archwire to be connected to or removed from the bracket.

2. The appliance of claim 1, which includes a pair of jaw members.

3. An orthodontic appliance for receiving an archwire comprising a base, a pair of jaw members pivotally and movably mounted on the base between open and closed positions, and spring means for coacting with the jaws to selectively lock the jaws into closed position and define with the base an archwire slot to lock the archwire to the bracket or in open position to allow the archwire to be connected to or removed from the bracket.

4. A self-ligating orthodontic bracket comprising:
a base mountable on a tooth,
a pair of jaws defining an archwire slot,
hinge means pivotally and movably hinging the jaws to the base such that the jaws are operable between an open position allowing insertion or removal of an archwire and a closed position for retaining the archwire,
and spring means engaging said jaws and operable for maintaining said jaws in said open or closed positions.

5. The bracket of claim 4, wherein means is provided on the base and jaws for locking the jaws in closed position.

6. The bracket of claim 5, wherein said locking means includes interengaging teeth on said base and jaws.

7. The bracket of claim 6, wherein opening of the jaws by movement of said spring requires movement of the jaws to disengage the teeth and then pivoting of the jaws to separate them from each other such that an archwire may be inserted between or removed from the jaws.

8. The bracket of claim 4, wherein the jaws include walls to receive a rectangular in cross section archwire so that a torquing force can be exerted on the bracket.

9. The bracket of claim 4, which further includes a plastic mounting pad molded to the base.

10. The bracket of claim 4, wherein said jaws are substantially L-shaped, and shaped to receive a rectangular archwire so that a torquing force may be applied to the bracket by the archwire.

11. The bracket of claim 4, wherein the bracket is metal.
12. The bracket of claim 4, wherein the bracket is ceramic.
13. The bracket of claim 4, wherein the bracket is plastic.
14. The bracket of claim 4, wherein said spring means includes a substantially flat spring member extending between the jaws at the hinge means.

15. The bracket of claim 4, wherein said hinge means includes lugs on the base meshing with lugs on the jaws, and hinge pins extending through said lugs.

16. The bracket of claim 15, wherein said hinge means further includes pin openings in the base lugs, and pin slots in said jaw lugs allowing the jaws to move and pivot on the hinge pin.

17. The bracket of claim 16, wherein said pin slots in said jaw lugs are substantially kidney shaped and oriented so as to allow the jaws to move between lock and unlock positions, where in the unlock position, the jaws may go to said open position.

18. A method of closing a self-ligating bracket and retaining an archwire on said self-ligating bracket wherein the bracket includes a base, a pair of jaws slidably and pivotally hinged to the base and movable between open and closed positions, and a spring member connected to the jaws, said method comprising the steps of:
placing the archwire against said spring member when the jaws are in open position, and
applying an inward force to the archwire to drive the jaws pivotally and slidably on the base to close the jaw members and lock the archwire to the bracket.

19. The method of opening a self-ligating bracket and releasing an archwire from said bracket, wherein the bracket includes a base, a pair of jaws slidably and pivotally hinged to the base and movable between open and closed positions, and a spring member connected to the jaws, said method comprising the steps of:
engaging said spring member with an instrument, and
applying an outward force to the spring member to drive the jaws slidably and pivotally into open position.

* * * * *